United States Patent [19]

Gauthier

[11] 4,367,562
[45] Jan. 11, 1983

[54] JOINT PROSTHESIS

[76] Inventor: Georges Gauthier, 85, cours Albert-Thomas, Lyon (Rhone), France

[21] Appl. No.: 274,259

[22] Filed: Jun. 16, 1981

[30] Foreign Application Priority Data

Jun. 19, 1980 [FR] France .................. 80 13915

[51] Int. Cl.³ .................. A61F 1/04; A61F 5/04
[52] U.S. Cl. .................. 3/1.91; 128/92 C
[58] Field of Search .................. 3/1.91, 1, 1.9; 128/92 C

[56] References Cited

U.S. PATENT DOCUMENTS

| | | | |
|---|---|---|---|
| 3,462,765 | 8/1969 | Swanson | 128/92 C |
| 3,593,342 | 7/1971 | Niebauer | 128/92 C |
| 3,681,786 | 8/1972 | Lynch | 3/1.91 |
| 3,875,594 | 4/1975 | Swanson | 3/1.91 |
| 4,204,284 | 5/1980 | Koeneman | 3/1.91 |
| 4,231,121 | 11/1980 | Lewis | 3/1.91 |
| 4,242,759 | 1/1981 | White | 3/1.91 |
| 4,313,232 | 2/1982 | Habal et al. | 3/1.91 |

*Primary Examiner*—Richard J. Apley
*Assistant Examiner*—David J. Isabella
*Attorney, Agent, or Firm*—Karl F. Ross

[57] ABSTRACT

An implantable joint prosthesis, e.g. to restore a joint between a distal bone and a proximal bone (for example a finger joint or toe joint) consists of a one-piece body of a material which is flexible and elastic (resilient) and has tapering projections extending in opposite directions from a central portion and adapted to be fitted into the respective bones. The central portion is formed at an intermediate location with a relatively thin region defining the articulation axis and with a pair of bulges which project in all directions transverse to the axis of the body outwardly of the respective projections on either side of this region and between the articulation region and the respective projection. The rounded bulge at the proximal side of the device is larger in volume than the rounded bulge at the distal side.

6 Claims, 2 Drawing Figures

JOINT PROSTHESIS

FIELD OF THE INVENTION

My present invention relates to a joint prosthesis and, more particularly, to an orthopedic implant adapted to replace a body joint and capable of being anchored to the bones which formed the original joint. The invention is most specifically directed to a prosthetic joint-replacement implant for replacing finger or toe joints although it can also be used to replace other articulations or joints of the body, such as the tarsus, carpus, sterno-clavicular or acromio-clavicular articulations.

BACKGROUND OF THE INVENTION

Body joints normally have two functions, the primary being to allow mobility while the secondary function is to transmit force.

The primary function enables, for example, a distal bone, e.g. some part of a distal appendage or digit, to assume a variety of positions vis-à-vis the proximal bone, digit or body member.

In the transmission of force, the joint acts mechanically to transfer forces from one bone to the other through the articulation, usually in directions which are perpendicular to the articulation surfaces. Thus the articulation or joint must be capable of force transfer in the manner described while allowing control of the relative movement of the bones.

However, it is important to note that the articulation, especially for certain body members, must also be capable of taking up or resisting support forces which may be perpendicular to the articulation axis, transverse to the articulation surfaces and even perpendicular to the axis of an artificial joint. Such support forces are those which are applied, for example, against the palm of the hand or the sole of a foot.

In conventional prosthetic devices for replacing the natural joints, the body has a flexible central region forming the articulation axis and extensions therefrom which are anchored in the respective bones. This central region has been found to have limited stability and transverse strength, i.e. to be insufficiently able to handle the longitudinal and transverse forces which may be applied to the prosthesis.

Even when the prosthetic device is capable of transmitting longitudinal force without difficulty, problems are nevertheless encountered when force is applied transverse to the longitudinal direction as is the case when pressure is applied to the palm of the hand or the sole of the foot. Frequently, moreover, an abnormal stress is applied to the articulation as when a finger or toe is bent backward. Here, too, conventional joint replacement implants have proved to be ineffective.

When abnormal stresses or abnormally directed stresses are applied to the flexible and elastic body, the deformation of the latter appears to be localized particularly at the junction between the extension and the bending zone, thereby tending to rupture the implant. The concentration of pressure which is also a characteristic of earlier systems, at locally weak or sensitive areas, can cause failure of the material with deterioration or instability of the prosthetic device and even discomfort.

OBJECTS OF THE INVENTION

It is the principal object of the present invention to provide a prosthetic device which avoids the drawbacks of the earlier systems described and which can be implanted with a long, useful life, a minimum of discomfort and little tendency to deteriorate.

Another object of this invention is to provide a prosthetic joint which not only is capable of allowing the relative movements of the bones spanned by the joint which are desirable, but also is capable of providing significant longitudinal and transverse stability with concomitant improvement in force-transmitting ability and high stability regardless of the direction in which a stress may be applied.

Still another object of the invention is to provide an improved prosthetic device for the purposes described which has an increased useful life.

SUMMARY OF THE INVENTION

These objects and others which will become apparent hereinafter are attained, in accordance with the present invention, in a joint prosthesis adapted to be anchored in two bones normally bridged by an articulation or joint, the prosthetic device being a one-piece body composed of a flexible and elastic (resilient) material, e.g. a biocompatible silicone rubber, and having a central body portion from which a pair of tapering projections extend to form roots, barbs, spurs or spikes adapted to be lodged within the respective bones. It is convenient to designate one of these extensions as a proximal extension at the proximal side of the prosthetic device while the other extension is a distal extension at the distal side of the device, the proximal and distal extensions being lodged respectively in the proximal and distal bones, e.g. of a proximal and distal digit on either side of a joint.

According to the invention, the body portion is formed at an intermediate region with the articulation and can be relatively thin in this zone which is flanked by a pair of bulbous or rotund bulges, each bulge being interposed between a respective projection and the articulation zone and extending in all directions perpendicular to the axis of the body, outwardly of the periphery of the respective projection at its junction with the bulge.

According to the invention, therefore, at each side of the thin zone of the central portion of the one-piece body, a rounded bulge is provided which extends outwardly in all directions so that its transverse dimensions exceed those of the respective extension and, at least in all directions transverse to the articulation axis, projects outwardly of the thin zone.

According to an important feature of the invention, the bulge at the proximal side of the device is significantly of greater volume than the bulge at the distal side.

It is also essential to the invention that the bulges have neither ridges nor notches or grooves, reentrant angles or like discontinuities on their surfaces or in the region of the junction of these bulges with the central or articulation zone or the respective projections. Thus there is no site at which the inception of breakage can be induced by such discontinuities.

While the terms "proximal" and "distal" have been used to describe the opposite sides of the device, it should be understood that these expressions are employed in their conventional biological sense. Thus the extension on the proximal side is generally longer than the extension on the distal side and of greater volume, being generally inserted into the large bone which is usually at the proximal side of the joint in the biological sense. The smaller bone receives the distal projection which can be shorter and of a smaller volume than the proximal projection. The proximal bulge is likewise larger than the distal bulge.

In the following description, moreover, reference will be made to directions and it is assumed, in order to simplify the description that the prosthetic device is implanted horizontally so that the flexure zone permits a vertical movement as in the case of a metatarsal-phalangeal joint with the foot flat on the ground. In practice, of course, the device can be inserted in any orientation.

According to a feature of the invention, the distal side of the bulge is convex in the direction of its extension with a curvature corresponding to the concave curvature at the end of the distal bone. The latter curvature corresponds to the osteoarticular concave surface which is part of a standard natural joint. By making the convex surface of the distal bulge complementary to the concave osteoarticular surface, a large contact area is provided for the support of the prosthesis against the distal osteocartilaginous material which guarantees longitudinal stability and, because of partial penetration of the convex distal bulge surface into the concave osteocartilaginous surface, excellent transverse and vertical stability.

Furthermore, the device of the invention avoids any need for resection of the distal bone since it is merely necessary to provide a central cavity in the latter corresponding in shape to the distal projection during the surgical implantation of the prosthesis. This reduces the risk of peripheral ossification around the prosthesis.

The reduction in the danger of ossification is a consequence of the fact that the distal portion of the prosthesis will contact substantially over its periphery an osteocartilaginous zone which has not been resected and thus is less susceptible to the development of hardened material (ossification). The osteocartilaginous surface is thus generally preserved in its natural state without roughening and thus without any traumatic effect vis-à-vis the patient or the prosthesis.

According to another feature of the invention, the proximal bulge of the prosthetic device has, at its side turned toward the supporting surface (e.g. the sole of the foot or the palm face of the hand) a protuberance of comparatively large volume (relative to the bulges on the opposite side) which forms a shoulder or surface at the junction between this protuberance and the proximal projection. This planar shoulder is inclined at an angle of 30° to 60° with respect to the longitudinal axis of the prosthesis. The inclination is such that the shoulder extends below the upper surface of the bone. The proximal bone is thus resected along a plane parallel to the plane of this shoulder, i.e. with a corresponding inclination. This arrangement has been found to further increase the stability of the joint. The lower large protuberance has been found to contribute to the comfort of the prosthesis when the palm or sole is pressed forcibly against a supporting surface and prevents any impediment to the tendons which control the flexure of the digit.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
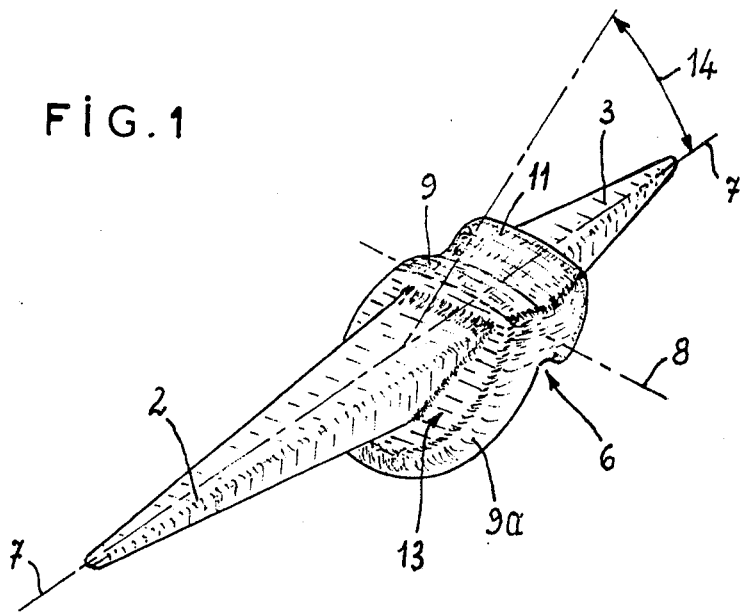
FIG. 1 is a perspective view of an implantable joint prosthesis according to the invention.

The prosthetic device shown in the drawing is a one-piece body or monoblock of a flexible but elastic material such as a biocompatible silicone elastomer. The prosthesis comprises a proximal projection 2 and a distal projection 3, each of which is of polygonal cross section (e.g. square) and tapers substantially to a point away from the central portion of the silicone rubber body.

The proximal projection 2 and the distal projection 3 are respectively intended to be inserted into complementarily shaped cavities formed in the proximal bone 4 and the distal bone 5 whose joint is to be replaced by the prosthesis.

Figure 2:
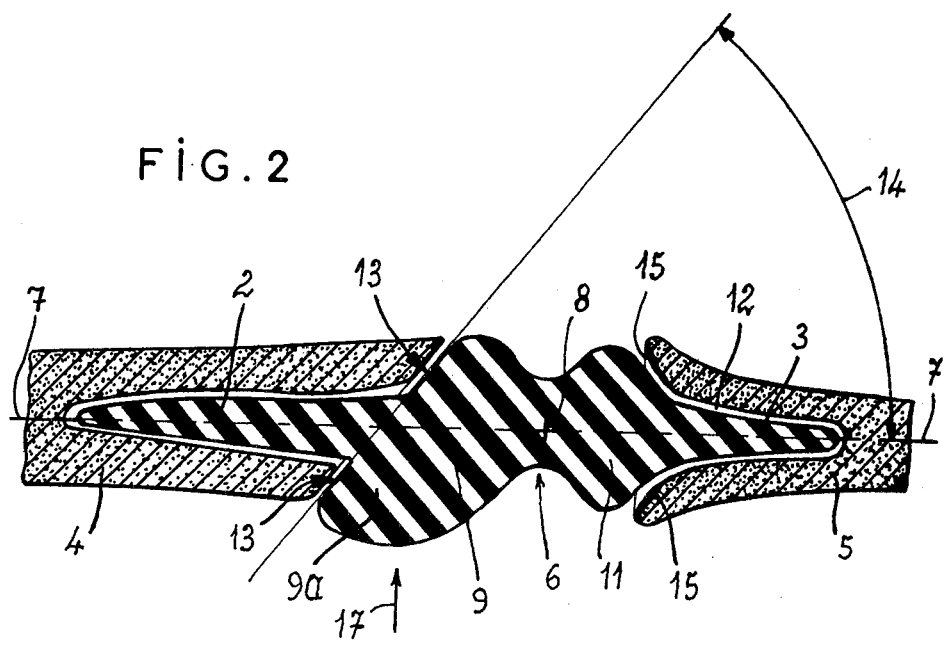
FIG. 2 is a section through this prosthesis diagrammatically illustrating its implantation between two bones.

At an intermediate location along the central portion of the body, i.e. the portion between the two projections, there is provided a thin zone 6 which has a thickness perpendicular to the longitudinal axis 7 of the prosthetic device and the plane of the paper in FIG. 2, constituting the narrowest part of the body portion and defining the articulation axis 8 which is likewise perpendicular to the longitudinal axis 7.

The narrow zone 6 is elongated in the direction of the articulation axis 8 as can be seen from FIG. 1 of the drawing.

To each side of the thin zone or articulation zone 6, the prosthesis is provided with a rounded or rotund bulge 9, 11.

The proximal bulge 9 is interposed between the projection 2 and the axis 8 while the distal bulge 11 is located between the axis 8 and the projection 3.

Because of the rounded configuration of these bulges, there are no discontinuities capable of constituting locations for the inception of breakage or tearing, the bulges together being of sufficient volume to impart to the prosthesis the desired degree of resistance to forces applied in any direction especially longitudinally and transversely.

Each bulge 9 or 11 has transverse dimensions, i.e. dimensions perpendicular to the axis 7 which exceed corresponding dimensions for the respective projections 2 and 3 so that these bulges project outwardly around the peripheries of the projections 2 or 3 at the junction of the projections with the bulges. In addition, at least transverse to the common plane of the axes 7 and 8, these bulges project further from the planes than the surfaces defining the thin zone 6.

The distal end face 11 of the central portion, turned toward the concave face of the articulation, is formed as a convex surface corresponding and complementary to the concave face 15 which can be the natural face formed by the osteocartilaginous tissue. The bone 5, therefore, need not be resected but need only be pierced to form the cavity 12 for the projection 3.

By eliminating the need to resect this bone and confining the projection to only one of the bones of the joint, namely, the proximal or larger bone, the traumatic dangers are reduced as are the dangers associated with ossification for the reasons stated.

The proximal bulge 9 is formed on its lower side, i.e. the supported side, with a protuberance 9a which can be significantly of greater volume than the remaining portions of the bulges, oriented to define a shoulder with an inclination at an angle 14 of about 45° with respect to the longitudinal axis 7. This inclination is such that the face 13 of the shoulder underlies the bone 4 which is resected so as to have a complementary inclination at its end receiving the projection 2.

A supporting force 17 thus is taken up initially by the protuberance 9a and can be transferred directly to the bone 4 without destabilization of the prosthetic device and without applying an undue stress upon the latter. As a result the prosthesis has excellent longitudinal, vertical and transverse stability and is most comfortable when applied and is particularly comfortable and effective when used for finger and toe joints.

I claim:

1. A joint prosthesis for the replacement of a joint between a proximal bone and a distal bone, said prosthesis comprising a unitary elongated body of a flexible, elastic and biocompatible material having a proximal projection receivable in said proximal bone, a distal projection receivable in said distal bone, and a body portion between said projections, said projections and said body being aligned along a common longitudinal axis in an elongate position of said prosthesis, said body portion being formed at an intermediate location therealong with a thin zone defining a transverse articulation axis substantially perpendicular to said longitudinal axis of said body and said projections, said body portion comprising a proximal rounded bulge between said thin zone and said proximal projection and a distal rounded bulge between said thin zone and said distal projection, said bulges being smooth, continuous and extending in all directions outwardly of said projections at the respective junctions of said projections with said bulges, said proximal projection having a greater volume than said distal projection.

2. The prosthesis defined in claim 1 wherein said distal bulge is formed with a convex surface complementary to a natural concave joint surface remaining on said distal bone.

3. The prosthesis defined in claim 1 or claim 2 wherein said proximal bulge has a large-volume protuberance extending to one side of said transverse axis corresponding to a supported surface of a joint formed by said prosthesis.

4. The prosthesis defined in claim 3 wherein said protuberance is formed with an inclined surface turned toward said proximal bone, said protuberance underlying said surface.

5. The prosthesis defined in claim 4 wherein said surface is inclined at an angle between substantially 30° and 60° with said axis and said proximal bone is resected to end in a surface complementary to said inclined surface.

6. The prosthesis defined in claim 5 wherein said body is composed of silicone rubber, said proximal projection is larger than said distal projection, each of said projections is of polygonal cross section, and said projections taper away from said body portion.

* * * * *